US010524861B2

(12) United States Patent
Beerwerth et al.

(10) Patent No.: US 10,524,861 B2
(45) Date of Patent: *Jan. 7, 2020

(54) HAIR REMOVAL DEVICE

(71) Applicant: Braun GmbH, Kronberg (DE)

(72) Inventors: Frank Beerwerth, Kaltenholzhausen (DE); Christian Neyer, Eschborn (DE); Dalibor Dadic, Koenigstein (DE); Felix Heinemann, Frankfurt am Main (DE)

(73) Assignee: Braun GMBH, Kronberg (DE)

( * ) Notice: Subject to any disclaimer, the term of this patent is extended or adjusted under 35 U.S.C. 154(b) by 46 days.

This patent is subject to a terminal disclaimer.

(21) Appl. No.: 15/419,214

(22) Filed: Jan. 30, 2017

(65) Prior Publication Data
US 2017/0215958 A1 Aug. 3, 2017

(30) Foreign Application Priority Data

Feb. 2, 2016 (EP) .................................... 16153813
Jan. 19, 2017 (EP) .................................... 17152185

(51) Int. Cl.
*A61B 18/18* (2006.01)
*H01L 25/075* (2006.01)
(Continued)

(52) U.S. Cl.
CPC .............. *A61B 18/18* (2013.01); *A45D 26/00* (2013.01); *A61B 18/1815* (2013.01);
(Continued)

(58) Field of Classification Search
CPC . A61B 18/18; A61B 2018/1807; A61B 18/20; A61B 18/203; A61B 2018/00315;
(Continued)

(56) References Cited

U.S. PATENT DOCUMENTS 6,663,659 B2 12/2003 McDaniel
8,961,578 B2 2/2015 Liu et al.
(Continued)

FOREIGN PATENT DOCUMENTS

WO WO-2006/005443 1/2006

OTHER PUBLICATIONS

European search report dated Jul. 22, 2016.
(Continued)

*Primary Examiner* — Ahmed M Farah
(74) *Attorney, Agent, or Firm* — Kevin C. Johnson

(57) ABSTRACT

The present invention is concerned with a hair removal device having a light emission unit having a substrate and a plurality of first LED dies that are mounted on the substrate on an area of at least 0.2 $cm^2$, in particular of at least 1 $cm^2$, the first LED dies having a peak emission wavelength in the far red or infrared wavelength range of between 700 nm and 980 nm, wherein the hair removal device is arranged to emit a treatment light pulse having a pulse length in the range of between 60 ms and 120 ms and the first LED dies have a radiant flux such that a radiant fluence on the skin of a user in the range of between 3 $J/cm^2$ and 7 $J/cm^2$ is achieved by application of the treatment light pulse.

13 Claims, 6 Drawing Sheets

(51) Int. Cl.
*H01L 33/48* (2010.01)
*H01L 33/60* (2010.01)
*H01L 33/62* (2010.01)
*H01L 33/64* (2010.01)
*A45D 26/00* (2006.01)
*A61B 18/00* (2006.01)
*H01L 31/147* (2006.01)

(52) U.S. Cl.
CPC ........ *H01L 25/0753* (2013.01); *H01L 33/486* (2013.01); *H01L 33/60* (2013.01); *H01L 33/62* (2013.01); *H01L 33/642* (2013.01); *A61B 2018/00476* (2013.01); *A61B 2018/1807* (2013.01); *H01L 31/147* (2013.01)

(58) Field of Classification Search
CPC .. A61B 2018/00452; A61B 2018/0047; A61B 2018/00476; A61N 5/06; A61N 5/0613; A61N 5/0616; A61N 5/0617; A61N 2005/0652; A61N 2005/0658; A61N 2005/0659; A61N 2005/0661; A61N 2005/0662
USPC ................ 606/3, 9–11; 607/88–92
See application file for complete search history.

(56) References Cited

U.S. PATENT DOCUMENTS

| | | | |
|---|---|---|---|
| 9,375,281 B2 | 6/2016 | Moench et al. | |
| 2004/0176823 A1* | 9/2004 | Island | A61B 18/203 607/88 |
| 2004/0191729 A1* | 9/2004 | Altshuler | A46B 15/0002 433/215 |
| 2005/0231983 A1* | 10/2005 | Dahm | A61C 19/003 362/294 |
| 2006/0206173 A1* | 9/2006 | Gertner | A61N 5/0616 607/88 |
| 2007/0038206 A1* | 2/2007 | Altshuler | A61B 18/203 606/20 |
| 2007/0185553 A1 | 8/2007 | Kennedy | |
| 2007/0198004 A1 | 8/2007 | Altshuler et al. | |
| 2007/0255355 A1* | 11/2007 | Altshuler | A61B 18/203 607/86 |
| 2009/0018621 A1 | 1/2009 | Vogler et al. | |
| 2010/0114007 A1 | 5/2010 | Fischer et al. | |
| 2010/0145321 A1 | 6/2010 | Altshuler et al. | |
| 2010/0196343 A1* | 8/2010 | O'Neil | A61B 18/203 424/94.4 |
| 2012/0116373 A1 | 5/2012 | Moench et al. | |
| 2012/0226268 A1* | 9/2012 | Liu | A61B 18/203 606/9 |
| 2014/0114231 A1* | 4/2014 | Rostro | A61N 5/062 604/20 |
| 2014/0303547 A1 | 10/2014 | Loupis et al. | |
| 2016/0287333 A1* | 10/2016 | Morrison | A61B 18/203 |
| 2017/0215959 A1* | 8/2017 | Beerwerth | A61B 18/18 |
| 2017/0215960 A1* | 8/2017 | Beerwerth | A61B 18/18 |
| 2017/0216619 A1* | 8/2017 | Beerwerth | A61N 5/0616 |

OTHER PUBLICATIONS

U.S. Appl. No. 15/419,229, filed Jan. 30, 2017, Frank Beerwerth et al.

U.S. Appl. No. 15/419,245, filed Jan. 30, 2017, Frank Beerwerth et al.

U.S. Appl. No. 15/419,254, filed Jan. 30, 2017, Frank Beerwerth et al.

* cited by examiner

HAIR REMOVAL DEVICE

FIELD OF THE INVENTION

The present invention is concerned with a hair removal device, in particular with a temporal hair removal device, comprising a plurality of LED dies.

BACKGROUND OF THE INVENTION

It is known that hair removal can be achieved with relatively high intensity light in order to achieve certain effects such as heat caused coagulation (i.e. denaturation) of certain portions (essentially proteins) of the hair cells leading to (temporal and/or permanent) hair removal (a.k.a. [temporal] hair growth reduction). Most known light based hair removal devices suitable for at least temporal hair removal make use of laser light sources or flash lamps as both light sources can provide high intensity light in short pulses. LEDs have generally been described as one alternative light source for skin treatment. The basic principle of this technology resides in the light absorption by melanin that is located in the hair follicle so that by heat dissipation from the heated melanin carriers into the surrounding tissue the complete hair follicle and, if desired, also the hair matrix can be heated so that the relevant proteins in the hair follicle/hair matrix are denatured via photothermolysis.

Document US 2012/0116373 A1 discloses a light application apparatus for applying light to an object. The apparatus comprises a light source for generating processing light and sensing light, where a control unit controls the light source such that processing light in a processing time interval and sensing light in a sensing time interval are generated alternately. The light source is preferentially a solid state light source, in particular a light emitting diode or a laser diode. It is preferred that the light source comprises a VCSEL. The processing light preferentially has a wavelength in the range of 570-1200 nm and an energy density in the range of 2-30 J/cm$^2$ and a pulse duration within 1 to 600 ms.

It is an object of the present disclosure to provide a hair removal device comprising a plurality of LED dies that is improved over the known devices or at least provides an alternative.

SUMMARY OF THE INVENTION

In accordance with one aspect there is provided a hair removal device comprising a light emission unit comprising a substrate and a plurality of first LED dies that are mounted on the substrate on an area of at least 0.2 cm$^2$, in particular of at least 1 cm$^2$, the first LED dies having a peak emission wavelength in the far red or infrared wavelength range of between 700 nm and 980 nm, wherein the hair removal device is arranged to emit a treatment light pulse having a pulse length in the range of between 60 ms and 120 ms and the first LED dies have a radiant flux such that a radiant fluence on the skin of a user in the range of between 3 J/cm$^2$ and 7 J/cm$^2$ is achieved by application of the treatment light pulse.

In accordance with one aspect there is provided method of cosmetic hair removal comprising the steps of providing a substrate on which a plurality of first LED dies is mounted on an area of at least 0.2 cm$^2$, in particular of at least 1 cm$^2$, which first LED dies are arranged for emitting light with a peak emission wavelength in the far red or infrared range of between 700 nm and 980 nm, in particular in the range of between 800 nm and 900 nm, and controlling the plurality of first LED dies to emit a treatment light pulse having a pulse length in the range of between 60 ms and 120 ms, in particular of between 80 ms and 120 ms, wherein the plurality of first LED dies is controlled to emit at a radiant flux such that a radiant fluence on the skin of a user in the range of between 3 J/cm$^2$ and 7 J/cm$^2$ is achieved by application of the treatment light pulse.

BRIEF DESCRIPTION OF THE DRAWINGS

The present disclosure will be further elucidated by a description of example embodiments in which description reference is made to figures. In the figures

DETAILED DESCRIPTION OF THE INVENTION

Figure 1:
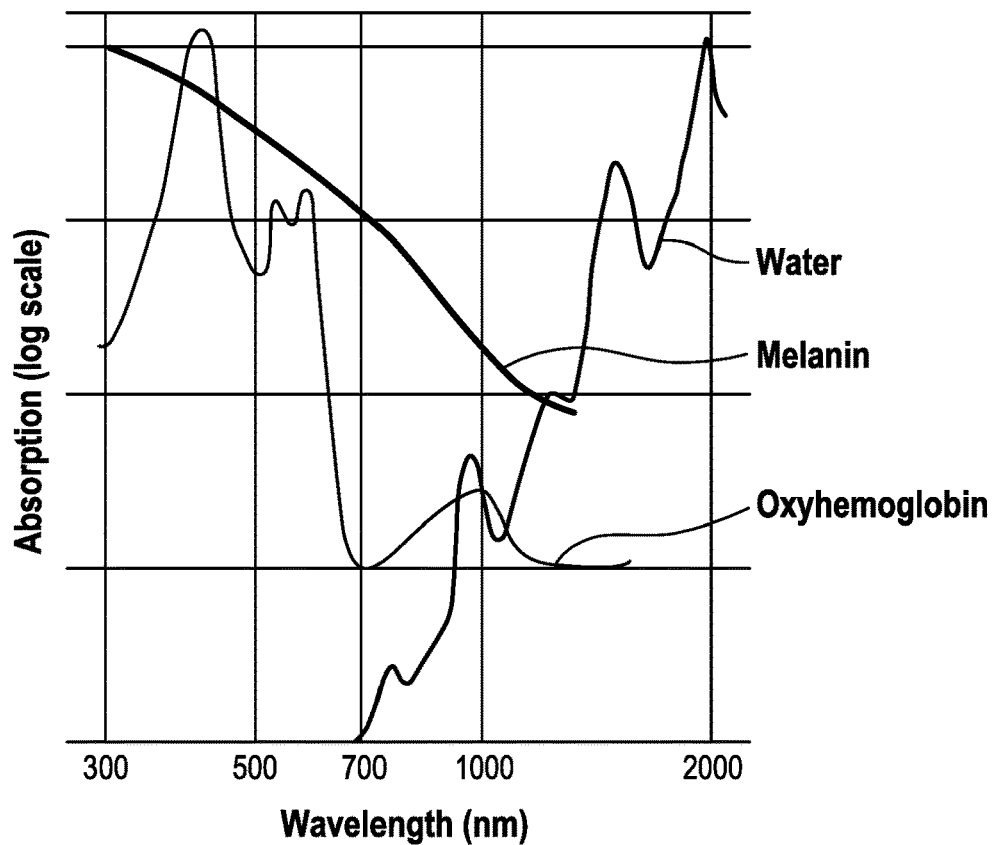
FIG. 1 is a graph showing the absorption coefficient for melanin, water, and oxyhemoglobin on a logarithmic scale vs. the wavelength of light between 300 nm and 2000 nm.

It is generally known that various types of skin treatment can be affected by applying light (in particular in the form of at least one treatment light pulse) to the skin. Such skin treatments encompass skin rejuvenation, wrinkle reduction, acne treatment, and (temporal and permanent) hair removal (also named hair growth reduction or hair growth management, as hairs are not necessarily immediately removed by the application of light), the latter application being the focus of the present disclosure. In particular, skin treatment for achieving temporal and/or permanent hair removal (hair growth reduction—in the following just "hair removal" is used) requires a radiant flux emitted by the LED die array per unit area that is much higher than the radiant flux that is required for skin rejuvenation or the like. For the application of treatment light pulses onto the skin various light sources have been discussed such as laser light sources, flash lamps (e.g. Xenon arc lamps), and semiconductor light sources such as LEDs. While laser light sources and flash lamps have been widely discussed with respect to hair removal, the application of LEDs as light source has been discussed in much less detail, in particular as the required radiant fluence to be applied on the skin within a short pulse length (e.g. below 10 ms) are easily delivered by lasers or flash lamps. Now, the present disclosure is directed to semiconductor light sources (where in the following the term LED is used, this shall encompass other surface emitting solid state light sources such as OLEDs), in particular arrays of LED dies (i.e. semiconductor dies in contrast to packaged LEDs), and their use for light-based temporal or permanent hair removal.

LED dies can emit light at essentially any wavelength from ultraviolet (UV) light to infrared (IR) light, i.e. from about 280 nm to 1300 nm, e.g. depending on the used semiconductor material. LED dies emit light with a relatively narrow spectral bandwidth of $\Delta\lambda \approx \pm \lambda/20$. Where in the present disclosure the term "wavelength" is used in relation to an LED die, this wavelength means the peak emission wavelength, i.e. the wavelength at the maximum of the light emission curve of the LED die.

In accordance with the present disclosure, the plurality of first LED dies emit light at a peak emission wavelength in the range of between 700 nm and 980 nm, in particular in the range of between 700 nm and 880 nm. Invisible light in the far red and infrared regime has a low absorption in blood and water while it still has sufficient absorption in eumelanin to cause sufficient heat generation in the hair follicles even with relatively long pulses. This light window is thus well utilizable for a large surface irradiation (in contrast to e.g. punctual laser light irradiation by which individual hair follicles are targeted) and home use application. Due to the long pulse times considered herein, the heat generation in the skin due to absorption of treatment light by melanin in the skin is kept relatively low even for somewhat tanned skin as the heat has sufficient time to dissipate from the small melanin granules into a large tissue volume. In some embodiments, the plurality of first LED dies emit light at a peak emission wavelength in the range of between 700 nm and 760 nm or in the range of between 820 nm and 880 nm. In some embodiments, a first sub-plurality of first LED dies emit light at a peak emission wavelength in the range of between 700 nm and 760 nm and a second sub-plurality of first LED dies emit light at a peak emission wavelength in the range of between 820 nm and 880 nm. In some embodiments, at least one further second LED die emits light at a peak emission wavelength in the visible light regime, i.e. in the range of between 400 nm and 700 nm. In some embodiments, an additional plurality of third LED dies (in addition to the plurality of first LED dies and alternatively also in addition to the at least one second LED die) emits light at a peak emission wavelength in the range of between 480 nm and 510 nm.

In some embodiments, the hair removal device has a control unit that is connected with the plurality of first LED dies for selectively activating the first LED dies (in addition the control unit may also be connected with, if present, any other LED dies for selectively activating the at least one second LED die and/or the third LED dies). The control unit may activate a first sub-plurality of first LED dies to emit a treatment light pulse, while a second sub-plurality of first LED dies is not activated, depending on e.g. a user-changeable setting (e.g. selection of an active area) or on a sensor signal provided from a sensor for measuring at least one skin property. The control unit may also be arranged for (a) selectively switching on or off at least one second LED die not during a treatment light pulse, or (b) switching on or off individual first LED dies during the treatment light pulse or at least during a portion of the treatment pulse, or (c) varying the magnitude of the forward current of at least one first LED die during the treatment light pulse.

In one aspect, the following description focuses on hair removal devices having a light emission unit with a plurality of substrate mounted first LED dies (which may be mounted in the form of a regular array pattern, but the LED dies may also be mounted in an irregular manner) that are able to deliver a radiant fluence in a range of between 3 J/cm² to 7 J/cm² by applying light pulses in a range of between 60 ms and 120 ms, in particular in a range of between 80 ms and 120 ms, by emitting a treatment light pulse in the far red to infrared wavelength range of between 700 nm and 980 nm. As will be explained in more detail, this combination of ranges is chosen for the hair removal of eumelanin carrying hairs by reducing the heat burden on tanned skin to a minimum, while guaranteeing that enough temperature is generated for a period as long as needed for low temperature coagulation of at least the relevant proteins in the hair follicle and optionally also of the hair matrix.

In the present disclosure, use is made of relatively long treatment light pulses, where the treatment light is in the wavelength range from far red to infrared of between 700 nm and 980 nm. It is known that the coagulation needed for bringing a hair follicle into apoptosis (programmed cell death) is a function of both, temperature and time. Hence, while a temperature exposure of 70 degrees Celsius over 1 ms leads to coagulation of proteins in a hair follicle, a temperature of 62 degrees Celsius leads as well to the needed coagulation if the hair follicle is exposed to this temperature over a period of 100 ms. While a pulse length of 60 ms and higher is considered to deliver a radiant fluence in the range of 3 J/cm² and higher, which is in particular used to treat brown hair on pale skin, treatment light pulses having a pulse length of at least 80 ms are considered, in particular for tanned skin. Thus, in accordance with at least one aspect, the hair removal device is arranged to emit at least one treatment light pulse having a pulse length of at least 60 ms (and in particular of below 120 ms), in particular a pulse length in a range of between 80 ms and 120 ms, and further in particular a pulse length of about 100 ms.

It seems appropriate to dwell on the particular technical effects of the chosen ranges. As has already been mentioned, coagulation of relevant proteins of the hair follicle or hair matrix, which is required for affecting hair growths reduction, can occur when applying a short treatment light pulse (e.g. 0.1 ms to 10 ms pulse) at a high radiant flux so that for a short period a high temperature is achieved at the location of the relevant proteins (typically, the heat generated in the melanin carriers must dissipate to the location of the proteins). Such treatment light pulses can easily be delivered by a high radiant flux light source, e.g. a laser or a flashlamp. LEDs are not able to deliver such high radiant flux pulses. It has now been discovered that also LEDs can be used for hair removal applications despite their low radiant flux, if the settings of the treatment light pulse are chosen such that the temperature achieved at the location of the relevant proteins is high enough to cause coagulation and the temperature is provided for a time long enough so that coagulation can occur. Light is absorbed by target chromophores, which typically are melanin for hair removal (here, the brownish eumelanin is the relevant target chormophore). The target chromophores heat up when absorbing treatment light. The heat dissipates into the tissue surrounding the chromophores. The temperature at a point in the tissue rises and eventually reaches into an equilibrium state of a constant temperature during the treatment pulse. The temperature needs to be above a threshold temperature for affecting protein coagulation during a given time period. The threshold temperature depends on the time period the respective temperature will be present, i.e. a higher temperature causes coagulation within a shorter period than a lower temperature. Obviously, there is an absolute threshold temperature below which protein coagulation is not caused even for very long exposure times. For treatment light in the far red to infrared regime in the range of between 700 nm and 980 nm (in particular in a range of between 820 nm to 880 nm, and further in particular for a wavelength of about 850 nm), a treatment pulse should last at least 60 ms and needs to deliver at least 3 $J/cm^2$ to affect effective hair removal (e.g. to generate relevant protein coagulation), while keeping the heat burden on the skin at an acceptable level. For hair removal, it may be desirable to heat also the hair matrix. As the hair matrix comprises essentially no target chromophore, the heat must dissipate from the hair follicle into the hair matrix, which requires a certain dissipation time. For LEDs in the given invisible wavelength range, the pulse length may thus be at least about 80 ms and may be up to about 120 nm and the pulse may deliver up to about 7 $J/cm^2$ in order to achieve a (low temperature caused) coagulation of the relevant proteins of the hair matrix. A pulse length above 120 ms at a fluence of between 3 to 7 $J/cm^2$ may not generate the necessary coagulation temperature (the radiant flux being too low) and increasing the fluence will lead to adverse side effects. It has further been found, that at a wavelength of about 850 nm, the fluence on the skin delivered by a 80 ms to 120 ms treatment light pulse may be in a range of between 5 $J/cm^2$ to 7 $J/cm^2$ for light brown to medium brown hair, while the fluence may be in a range of between 3 $J/cm^2$ to 5 $J/cm^2$ for dark brown hair.

Thus, while documents like the before mentioned US 2012/0116373 A1 disclose broad ranges of 1 ms to 600 ms pulse length and 2 $J/cm^2$ to 30 $J/cm^2$ fluence in a general manner for a broad range of light sources emitting light with wavelength in a range of between 570 nm to 1200 nm, the herein proposed much narrower ranges of 60 ms to 120 ms pulse length at a fluence in the range of between 3 $J/cm^2$ to 7 $J/cm^2$ for LEDs emitting in the wavelength range from far red to infrared light provide a narrow range for very efficient hair removal resulting in "low temperature" protein coagulation. In addition, the stretch of the pulse length to these very long pulse lengths (at the given fluences) also lowers the heat burden on the skin and thus skin with higher melanin content can be treated than with lower pulse lengths.

At least some of the LED dies mounted on the substrate have a mounting density and light output power (radiant flux) that is sufficient to affect at least temporal hair removal. This will be explained more in detail in following paragraphs.

In one aspect, the following description focuses on hair removal devices that comprise a light emission unit with substrate mounted LED dies comprising a plurality of first LED dies arranged for emitting at a first wavelength in the far red to infrared range (e.g. at 850 nm). In another aspect, the following description is focusing on hair removal devices that comprise a light emission unit with substrate mounted LED dies comprising a first sub-plurality of first LED dies arranged for emitting at a first wavelength (e.g. 850 nm) and a second sub-plurality of first LED dies emitting at a second wavelength different to the first wavelength (e.g. 730 nm). In some embodiments, at least the first sub-plurality of the first LED dies has a mounting density and light output power (radiant flux) sufficient for affecting at least temporal hair removal. In some embodiments, at least a second LED die may be arranged to emit visible light at a lower radiant flux sufficient for illumination purposes (e.g. the first LED dies emit at a not visible light wavelength above about 700 nm and the second LED die emitting visible light may be used for visually indicating that a treatment light pulse is being emitted). As different LED dies can easily be mounted on the same substrate, first LED dies arranged for treatment and at least one second LED die arranged for illumination can be arranged on the same mounting area and can be separately controlled by respective individual wiring. In some embodiments, LED dies of the same kind are controlled as a group instead of being individually controlled. In particular, LED dies can be arranged in series and can then be controlled as a group. LED dies of a single row or column of an array of LED dies may thus be connected in series, but of course the position of the LED dies that should be controlled at the same time is arbitrary.

For sake of completeness, where the present disclosure uses the term "pulse length", this time period means the pulse length measured at full-width-half-maximum (FWHM) pulse intensity.

While the "radiant fluence" is here provided as a value on the skin of the user, it is to be understood that the hair removal device as described herein either has the LED dies located essentially at the level of an exit opening or the substrate area mounted with LED dies is surrounded by a casing having reflective inner walls, so that the radiant fluence received by the skin of the user (during regular operation) means the radiant fluence that is measured at the level of the LED dies because the substrate area to which the LED dies are mounted is substantially of the same size as the area of the skin treated. In cases, where the light emitted by the LED dies is applied on the skin with a diverging beam that is not spatially limited by a reflective casing, the respective reduction factor needs to be taken into account (i.e. the radiant fluence at the LED dies level must be respectively higher than the herein defined radiant fluence on the skin).

In contrast to a flash lamp, an LED die emits in a relatively narrow wavelength band (e.g. with a spectral bandwidth (FWHM) of $\Delta\lambda \approx \pm \lambda/20$). Thus, similarly to a laser, LED dies can be chosen such that the light emitted is optimal for the particular situation (e.g. determined by hair color and/or skin color). Hence, there is no need for optical filters that are typically used in IPL (Intense Pulsed Light) devices using a flash lamp, where the flash lamp emits in a very broad wavelength spectrum including UV portions that are to be filtered out for known health reasons.

In one aspect of the present disclosure, a hair removal device comprises different LED dies arranged for emitting at different wavelengths, e.g. at two different wavelengths, three different wavelength etc. On the one hand, at least one further LED die arranged for emitting at a visible wavelength can be used to visually indicate to the user the on/off state of the device, as the device is arranged to emit a treatment light pulse in the invisible light wavelength range (i.e. in the far red or infrared (IR) light regime). On the other hand, LED dies emitting at different wavelengths can be used to optimally tune the wavelength for a particular situation (e.g. changing hair color and/or skin color from user to user or even for a single user, where in particular skin color depends on the tanning of the treatment area). These possibilities will be explained in more detail below.

In essence, light based hair removal aims to reduce or inhibit hair growth by thermally affecting the hair follicle without affecting the surrounding skin. In order to thermally affect the hair follicle, light must be absorbed by a target chromophore in the hair follicle. Generally, the target chromophore is melanin (i.e. typically the brownish/blackish eumelanin, but also the reddish pheomelanin, which is mostly present in red hair). FIG. 1 shows the relative light absorption of melanin, oxyhemoglobin (blood), and water on a logarithmic scale in a range of between 300 nm and 2000 nm (the absorption curves of FIG. 1 are taken from: Christine C. Dierickx, M. D. "*Laser Hair Removal: Scientific Principle and Practical Aspects*", Lumenis, 2002—www.lumenis.com). Heat generated in the melanin carrying portions of the hair follicle dissipates into the surrounding tissue and eventually leads to coagulation of proteins if the heating time and the temperature together are above a certain threshold, where—as had been explained—the temperature leading to coagulation is lower if the heating time is longer.

Figure 2:
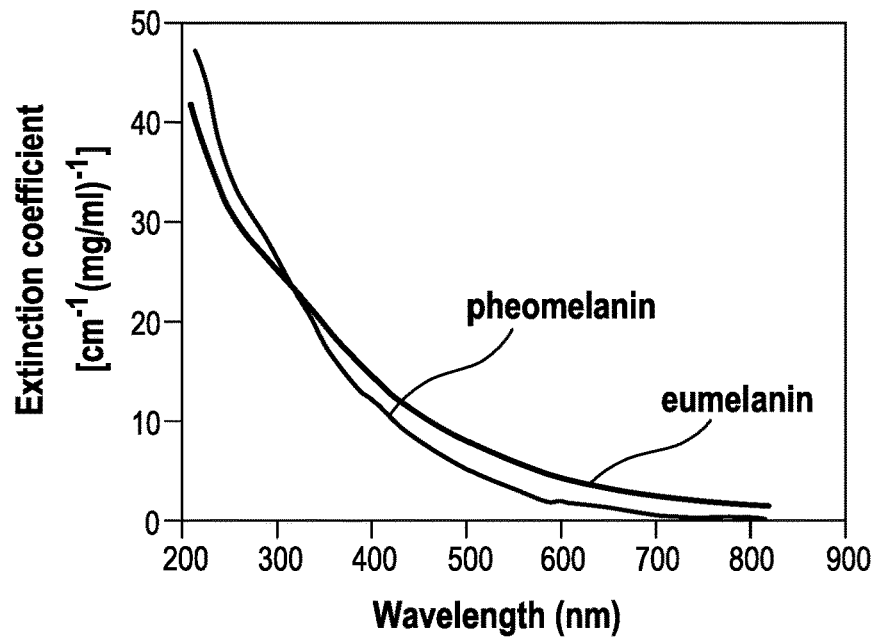
FIG. 2 is a graph showing the extinction coefficient of eumelanin and pheomelanin vs. the wavelength of light between 200 nm and 900 nm.

The present disclosure is essentially directed to a large area hair removal device (e.g. a treatment area of at least 0.2 $cm^2$, in particular of around 1 to 4 $cm^2$, and potentially up to about 10 $cm^2$) and to unmonitored home use (i.e. allowing a user to perform the treatment at home without the risk of injuring and without the need of professional support by medically trained personnel). Such a hair removal device illuminates large skin areas without particularly addressing individual hair follicles. That means that also skin tissue without hair follicles is irradiated by the treatment light pulse as well as blood vessels being present in the dermal tissue. In order to leave skin tissue and blood vessels thermally relatively unaffected (i.e. to keep the thermal effect on skin tissue and vessels at a level acceptable for home use) in such large area treatment, optimal hair follicle treatment occurs in wavelength ranges in which the melanin absorption is high over the absorption in water and by oxyhemoglobin. Thus, for brownish/blackish hair that carries eumelanin (including blonde hair, i.e. fair brownish hair), a particular efficient wavelength range is between 700 nm and 980 nm, where the absorption by water and oxyhemoglobin is low in comparison to melanin. Hair removal by light application becomes difficult if eumelanin is essentially missing as chromophore and only pheomelanin can be targeted (i.e. in case of red hair), as the absorption curve for pheomelanin lies below the curve for eumelanin. FIG. 2 show the (mass) extinction coefficient curves for eumelanin and pheomelanin (taken from: T. Sarna, H. M. Swartz, *The physical properties of melanins*, in "The Pigmentary System", ed. J. J. Nordlund et al., Oxford University Press, 1988). The extinction coefficient is a parameter that defines how strongly a substance absorbs light of a certain wavelength. FIG. 2 shows that a treatment light pulse of a certain radiant fluence in the wavelength range of between 700 nm to 980 nm has less an effect on red hair and thus cannot generate a temperature in the hair follicles that is sufficiently high to cause protein coagulation. It is thus believed that red hair is best treated by applying light at a wavelength of around 500 nm (e.g. in a wavelength range of between 480 nm and 510 nm), where oxyhemoglobin has a local absorption minimum (see FIG. 1).

A major factor in setting the right parameters for light based hair removal is the understanding of the absorption of light by the melanin in the skin and the thermal burden on the skin depending on the melanin content of the skin. Melanin content of the skin, i.e. skin color, is generally related to the Fitzpatrick skin type (FST) classification scale, by which FST type I (pale white) to FST type VI (deepest pigmentation) skin types are determined. The more intense the skin color, the higher is the melanin content in the skin and the higher is the light absorption by the melanin particles in the skin and thus the higher is the thermal burden on the skin. Melanin particles in the skin have a typical size in the range of 1 µm to 5 µm, whereas hair follicles have a size in the range of 100 µm to 300 µm. The substantial difference in the size of the melanin carriers (melanin carrying portion of the hair follicles vs. melanin granules in the skin) leads to a different heat dissipation behavior. While the mentioned melanin granules in the skin have a thermal relaxation time of below 0.1 ms, hair follicles have a thermal relaxation time of around 10 ms. Now, it is generally believed that a certain radiant fluence (light energy per unit area) needs to be applied within a certain time frame in order to thermally affect hair follicles. It is believed that the pulse length shall have a value that is above the thermal relaxation time of the melanin granules in the skin in order to allow heat to dissipate from these melanin particles and to reduce the thermal burden on the skin due to light absorption by the pigments. The pulse length may thus in particular be ten times higher than the thermal relaxation time (i.e. at least about 1 ms or above). For pale to medium skin color (FST I-III) the effect of the light absorption of melanin in the skin leads to limited thermal influence and does not play a major role in the determination of optimal pulse length. Anyhow, such short light pulses of 1 ms or even below of a sufficient fluence cannot be generated by today's LED dies even if mounted with a high density as described herein. In accordance with the present disclosure, a pulse length of at least about 60 ms is considered for reasons explained above, which go beyond the mere radiant flux limitation of today's LED arrays. If the necessary radiant fluence is provided in a too long treatment light pulse, heat dissipation reduces the temperature that can be achieved in a hair follicle to a value too low for effective protein coagulation to occur in the hair follicle. It is believed that the pulse length should not be longer than about 120 ms, as otherwise the necessary temperature for ("low temperature") coagulation will not be reached (for the fluence values in the range of between 3 and 7 $J/cm^2$). The radiant fluence delivered during this time period with a pulse in the far red to infrared wavelength range shall be in the range of between 3 $J/cm^2$ to 7 $J/cm^2$ in order to achieve an effect relevant for at least temporal hair removal (i.e. a thermally affected change in at least the hair follicle so that a temporal or permanent hair growth reduction occurs). As mentioned, the hair removal device may be arranged to emit a treatment light pulse with a pulse length in the range of between 80 ms and 120 ms, as 80 ms and beyond may provide for an even better hair removal effect, in particular for heating of the hair matrix.

Another factor that is to be taken into account is the penetration depth of the light into the skin. The optical penetration depth (distance where the intensity of the light is reduced to 1/e) seems to vary in literature. E.g. for fair Caucasian skin values of 0.230 mm at a wavelength of 500 nm to about 1.6 mm at a wavelength of 1000 nm are provided in one reference (R. Rox Anderson et al., The Optics of Human Skin, The Journal of Investigative Dermatology, 77: 13-19, 1981), while values of about 0.9 mm for 500 nm and 2.6 mm at 1000 nm are provided by another reference (Bashkatov, et. al.; Optical properties of human skin, subcutaneous and mucous tissues in the wavelength range from 400 to 2000 nm; J. Phys. D: Appl. Phys. 38 (2005) 2543-2555). Independent from these differences, the penetration depth generally considerably decreases from a wavelength of 1000 nm to a wavelength of 500 nm. Hair follicles are located at around 1-3 mm below the skin surface. Thus, wavelengths believed optimal for red hair treatment have a particularly low penetration depth. The low penetration depth of low wavelength light also excludes using light of even lower wavelength, e.g. UV light of around 300 nm, which essentially would not even reach the hair follicles, besides other risks involved with UV light. Because of the strong absorption of light around 500 nm in the skin tissue, it is believed that a radiant fluence in a range of between 3 $J/cm^2$ to about 6 $J/cm^2$, in particular in a range of between 3 $J/cm^2$ to 5 $J/cm^2$, is to be applied.

As has been mentioned before, a light emission unit in accordance with the present disclosure has a substrate on which a plurality of LED dies each having a certain radiant flux per LED die is mounted at a sufficiently high density (e.g. between about eight to about 90 LED dies per square centimeter, but the achievable density expressed in number of dies per unit area naturally also depends on the size of the LED dies). Some examples of LED dies suitable in accordance with the disclosure are discussed in the following.

In a first example, a plurality of first LED dies is mounted on a substrate, where each first LED die of the plurality is arranged to emit in a wavelength range of between 700 nm and 780 nm. One example of an LED die emitting in this range is the LED die used in the OSLON SSL® 150 (GF CSHPM1.24—datasheet Version 1.0) from Osram GmbH, Munich, Germany. The respective LED die emits light at a peak emission wavelength of 730 nm (far red) with a spectral bandwidth (FWHM) of $\Delta\lambda=\pm 30$ nm. This LED die has a radiant flux (also called radiant power) of between 201 mW and 280 mW (typical 231 mW) at a forward current of 350 mA, where a forward current of up to 1000 mA is specified (leading then to a typical radiant flux of 660 mW).

These LED dies from Osram (having a die size of about 1 mm×1 mm=1 $mm^2$) may be mounted on a substrate with a distance of about 0.2 mm so that 8 times 8=64 LED dies can then be mounted on a 1 cm times 1 cm=1 $cm^2$ substrate area.

Generally, large size LED dies may have a size in the range of between 0.5 mm to 1.5 mm times 0.5 mm to 1.5 mm (i.e. an area of 0.25 $mm^2$ to 2.25 $mm^2$). LED dies may be connected to the substrate by wire bonding (in particular gold wire bonding), but in order to achieve a high packaging form factor and enhanced heat dissipation, LED dies may also be connected to the substrate via flip chip technology (a density of 89 1×1 $mm^2$ LED dies per square centimeter may thus be achieved). Driving the above mentioned Osram LED dies (density of 64 LED dies per square centimeter) at the specified forward current of 1000 mA to emit a treatment light pulse having a pulse length of between 60 ms to 120 ms leads to a radiant fluence on the skin (assuming that all radiant energy is applied onto a skin area of the same treatment area size as the mounted substrate area size) in a range of between 2.534 $J/cm^2$ and 5.068 $J/cm^2$ (at a density of 89 LED dies per square centimeter, a fluence of 7.05 $J/cm^2$ can be achieved). Excess heat generated by the LED dies while emitting light pulses can be dissipated away from the substrate by a passive or active cooling arrangement, e.g. a heat sink, heat pipe, or an active liquid cooling system. Passive cooling arrangements (e.g. heat sinks) may be supported by providing an (cooled) air stream). The efficiency of LED dies often is around 30%, so that a treatment light pulse generating a radiant fluence of 7 $J/cm^2$ means that about 16.3 $J/cm^2$ of excess heat must be dissipated. In contrast to flash lamps that require a certain cooling down time of about 1 s and more, LED dies can be pulsed at a higher frequency and thus a faster overall treatment time of a large skin area can be achieved with LED dies.

In the above described first example, at least one LED die from the eight times eight LED die array may be replaced by a different LED die (a second LED die) emitting at a second wavelength different to the first wavelength in the visible range of between 400 nm and 700 nm and the fluence on the skin would than still essentially cover a range of between 3 $J/cm^2$ and 7 $J/cm^2$ for a pulse length of between 60 ms and 120 ms.

In a second example, the LED dies may be taken from the OSLON Black Series (850 nm) from Osram GmbH, Munich, Germany. In accordance with the data sheet (Version 1.1 from 2014-01-09), the respective LED die (size 1×1 $mm^2$) emits light at a peak emission wavelength of 860 nm (centroid wavelength: 850 nm) with a spectral bandwidth (FWHM) of $\Delta\lambda=\pm 30$ nm. The total radiant flux is given as 1030 mW at a forward current of 1000 mA. Already eight such LED dies mounted on a substrate area of 1 $cm^2$ lead to a radiant fluence of about 1 $J/cm^2$ per 120 ms pulse length on a skin treatment area of 1 $cm^2$ (assuming that the total radiant flux of the LED die is applied onto the skin treatment area).

In a third example, again an array of 8×8 LED dies is mounted on a substrate area of 1 $cm^2$. A first sub-plurality of 44 first LED dies (OSLON SSL® 150 emitting at a first wavelength of 730 nm) is essentially mixed with a second sub-plurality of 20 first LED dies (OSLON Black Series emitting at a second wavelength of 850 nm). If only the first LED dies are switched on to emit a treatment light pulse of 120 ms, a fluence of about 3.5 $J/cm^2$ can be achieved. If only the second LED dies (850 nm) are switched on to emit a treatment light pulse of 120 ms, a fluence of almost 3 $J/cm^2$ can be achieved. Switched on together, a fluence of almost 6 $J/cm^2$ can be achieved in a 120 ms treatment light pulse.

In addition, the hair removal device may comprise Golden DRAGON Plus LV W5AM LED dies from Osram GmbH, Munich, Germany, which emit light at a peak emission wavelength of 502 nm (typical dominant wavelength of 505 nm). In accordance with the datasheet (version 1.1), the LED die has a luminous flux of 67 lm at a forward current of 350 mA. 67 lm convert to a radiant flux of about 240 mW for a wavelength of 505 nm (about 684 mW at 1000 mA forward current when a linear extrapolation is used). As the 505 nm dominant wavelength LED die emits in a spectral band around the dominant wavelength and as the lumen to Watt conversion is strongly depending on the wavelength, this value is just an estimate. Around twenty-one such 505 nm LED dies are needed per square centimeter to achieve a radiant fluence of about 3 $J/cm^2$ in a 200 ms treatment light pulse. Hence, about forty-four 505 nm LED dies per square centimeter provide the radiant fluence of 3 $J/cm^2$ in a 100 ms pulse and about eighty-eight 505 nm LEDs provide a radiant fluence about 6 $J/cm^2$ in a 100 ms pulse. About eighty-eight 505 nm LED dies can provide a radiant fluence of about 3 $J/cm^2$ in a 50 ms pulse. The hair removal device may comprise a plurality of such LED dies in order to additionally provide red hair treatment capability.

It is to be understood that the values discussed here are relatively rough reference values, as the radiant flux of an LED die depends on the temperature of the LED die, the forward current and other factors.

Table 1 is a summary of wavelength, pulse length and fluence values that the inventors of the present description believe to represent optimal treatment parameters for the given hair color and FST skin type. The wavelength is understood to be a representation of a wavelength range in each case, which should cover a range of ±50 nm (optionally ±30 nm) around the given single wavelength value. It is noted that in some embodiments the hair removal device comprises a first sub-plurality of first LED dies arranged for emitting light with a peak emission wavelength around 730 nm and a second sub-plurality of first LED dies arranged for emitting light with a peak emission wavelength around 850 nm so that a control unit can activate the LED dies in accordance with Table 1 (excluding the red hair situations). Additionally, a plurality of third LED dies arranged for emitting light with a peak emission wavelength around 500 nm may be present (e.g. arranged on an additional substrate), so that the control unit can activate the LED dies in accordance with Table 1.

TABLE 1

Wavelength, fluence and pulse length values provided as a function of hair color and FST skin type. It is to be understood that the wavelength shall represent a range of wavelengths of ±50 nm around the given single wavelength value.

| Hair color | Skin Type [FST] | Wavelength [nm] | Pulse length [ms] | Fluence [J/cm$^2$] |
|---|---|---|---|---|
| Light brown/medium | I-II | 730 | 60-120 | 4-7 |
| Dark brown | I-II | 730 | 60-120 | 3-5 |
| Red | I-II | 500 | 30-200 | 3-6 |
| Light brown/medium | III-IV | 730 + 850 | 60-120 | 4-7 |
| Dark brown | III-IV | 730 + 850 | 60-120 | 3-5 |
| Red | III-IV | 500 | 100-200 | 3-6 |
| Light brown/medium | V-VI | 850 | 60-120 | 4-7 |
| Dark brown | V-VI | 850 | 60-120 | 3-5 |
| Red | V-VI | — | — | — |
| White/grey | All | — | — | — |

Figure 3:
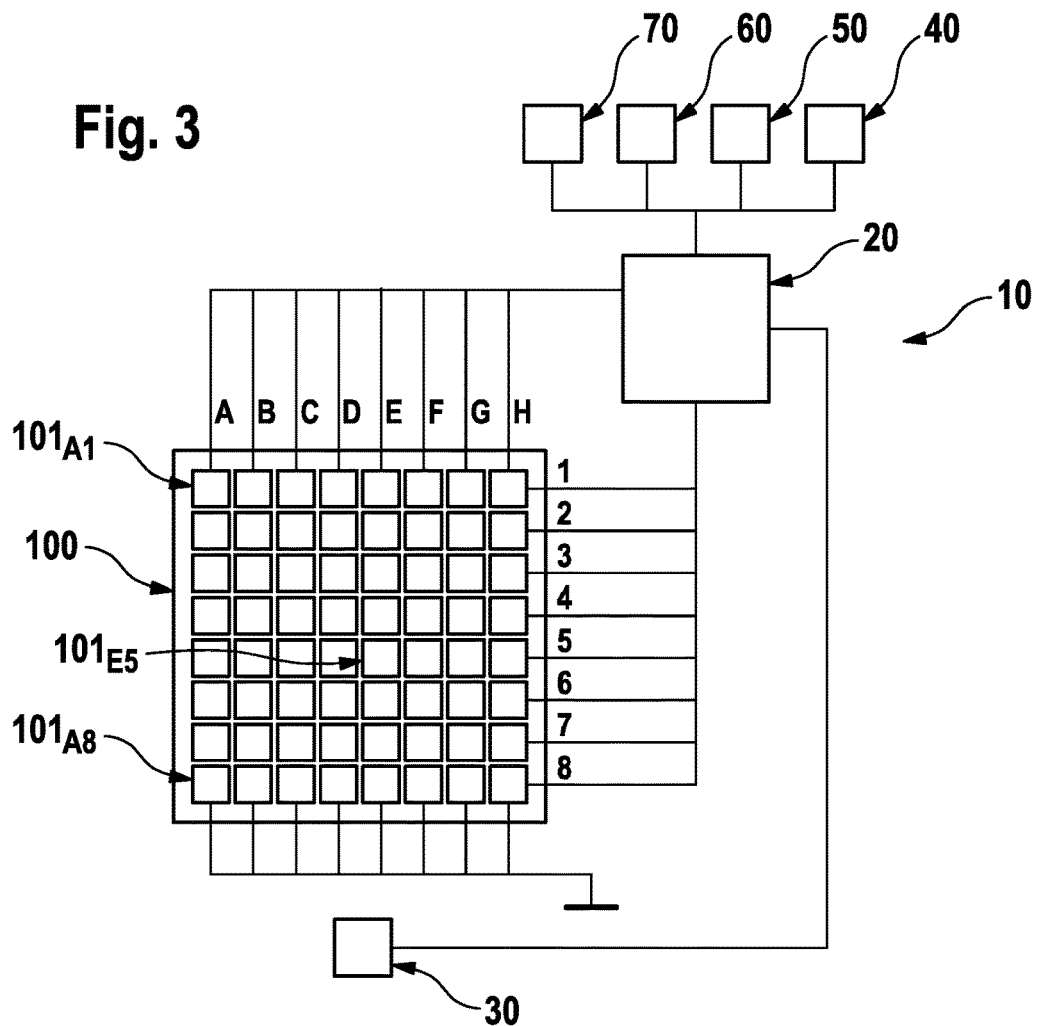
FIG. 3 is a schematic depiction of an example embodiment of a light emission unit in accordance with the present disclosure, which comprises a substrate on which an eight times eight matrix of first LED dies is mounted.

FIG. 3 is a schematic depiction of an example embodiment of a light emission unit 10 in accordance with the invention. The light emission unit 10 comprises a substrate 100 on which a plurality of 64 LED dies are mounted. The LED dies are arranged in a regular rectangular 8 times 8 pattern in columns A to H and rows 1 to 8, so that the LED dies can be identified by their position in the column-row matrix. Three LED dies $101_{A1}$, $101_{A8}$, and $101_{E5}$ are exemplary identified and it shall be understood that LED dies in a matrix arrangement can be identified by their column and row added as a suffix to the respective reference numeral.

Figure 4A:
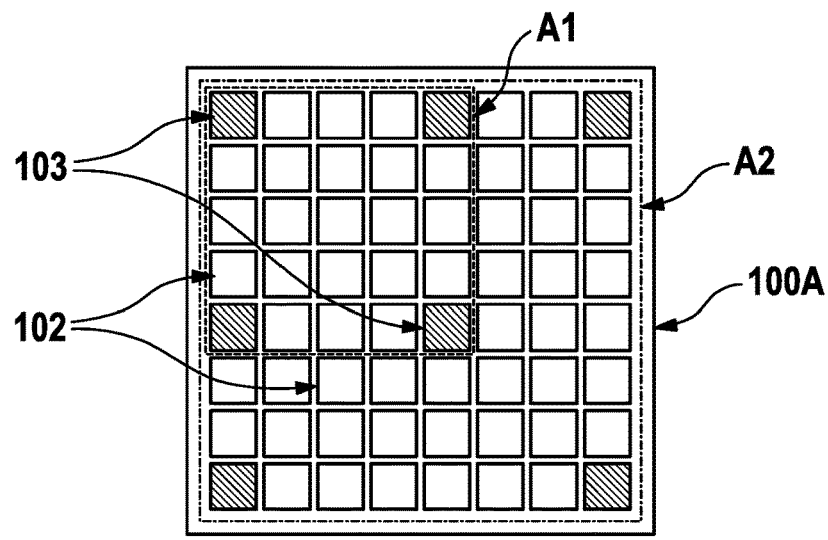
FIG. 4A is another example embodiment of an eight times eight matrix of LED dies mounted on a substrate comprising pluralities of first and second LED dies.
Figure 4B:
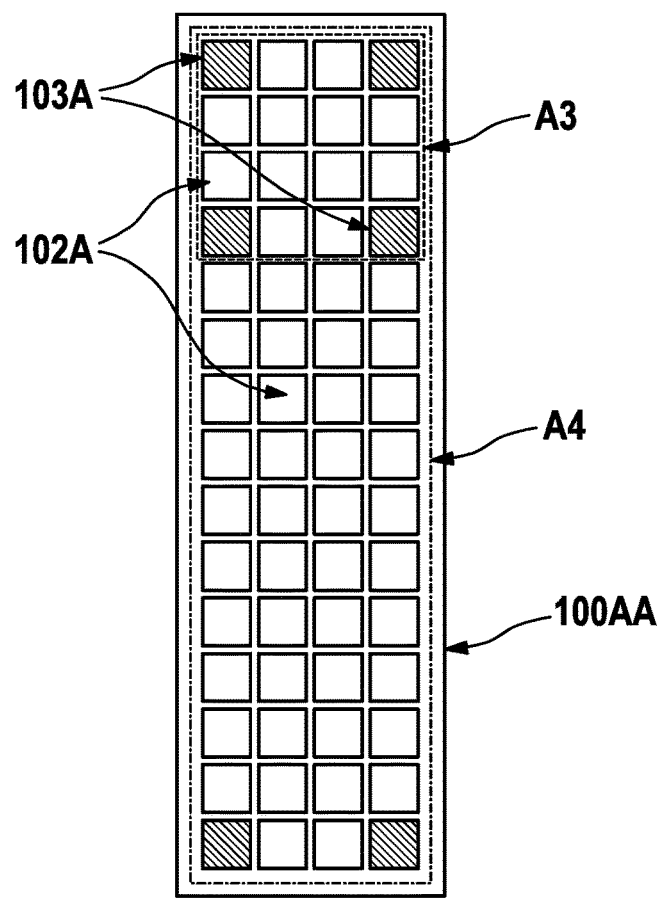
FIG. 4B is an example embodiment of a fifteen times four matrix of LED dies mounted on a substrate comprising pluralities of first and second LED dies.
Figure 5:
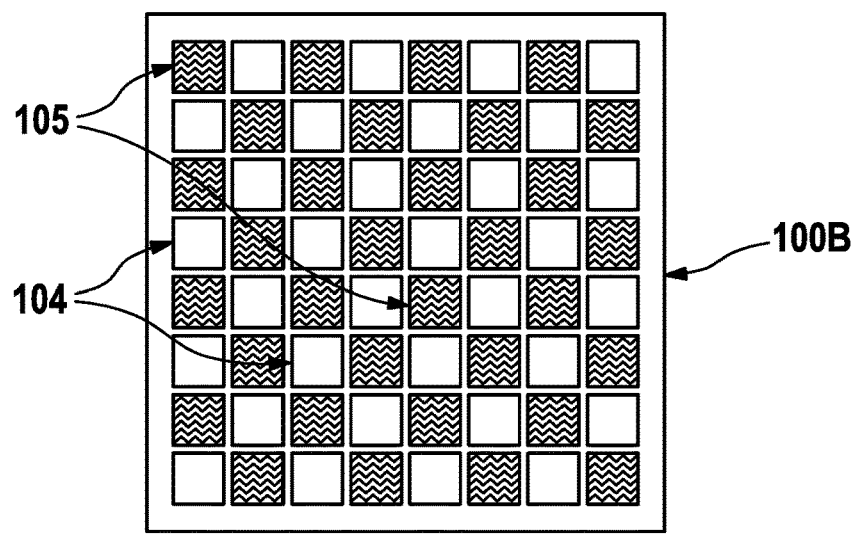
FIG. 5 is another example embodiment of an eight times eight matrix of LED dies mounted on a substrate comprising pluralities of first and second LED dies.
Figure 6:
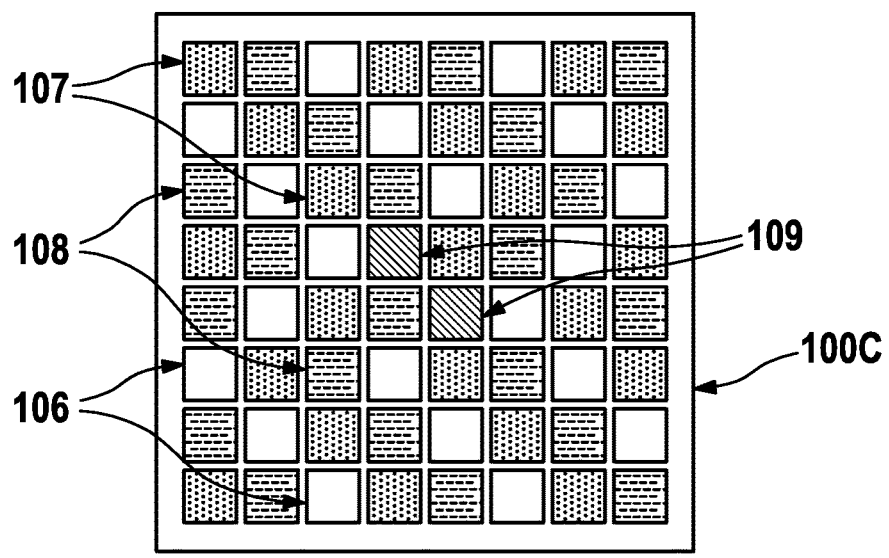
FIG. 6 is a further example embodiment of an eight times eight matrix of LED dies mounted on a substrate comprising four different pluralities of LED dies.

It is to be understood that the shown 8 times 8 square LED die matrix is just an example and the LED dies may be arranged on the substrate in any sensible manner, either as a regular square or rectangular matrix such as a 2 times 2, a 2 times 4, a 3 times 6, a 5 times 5, a 10 times 14, a 4 times 15 (see FIG. 4B) etc. matrix or in a less structured, more random pattern. Instead of being arranged in a regular square or rectangular matrix, the LED dies may be arranged in a regular pattern, which resembles a circular region rather than a square or rectangular region. Any other shape of the mounted substrate area may be chosen as well (e.g. triangular, trapezoidal, arbitrary). In the examples of FIGS. 4A, 5 and 6, the same 8 times 8 matrix will be used for sake of simplification of the discussion, but the concepts and ideas described with respect to these figures are of course also applicable to the just mentioned other regular or irregular patterns of substrate mounted LED dies. FIG. 4B shows an embodiment with a 4 times 15 matrix.

A control unit 20 has leads connected with the matrix of LED dies in order to selectively provide voltage and current supply to each of the LED dies 101. As mentioned before, the 8 times 8 matrix has 8 columns of LED dies that are connected in series so that each of the columns is controlled at the same instant. Generally, while the control unit 20 may be arranged to simultaneously switch on and off all LED dies, the control unit 20 may also be arranged to individually switch on or off each of the LED dies mounted on the substrate. Generally, a control unit may be connected with the plurality LED dies in any suitable manner. All of the LED dies of the 8 times 8 matrix may be arranged as first LED dies emitting at a given first wavelength in the far red to infrared wavelength range of between 700 nm and 980 nm, but—as also discussed below—some of the LED dies in such a matrix may be realized as different LED dies.

Control unit 20 is coupled with a sensor 30 for measuring a skin property, e.g. the skin color (pigmentation level). The sensor may comprise a light source that is illuminating the skin and the sensor may be arranged to determine the skin property such as skin color from the amount of light that is backscattered to the sensor (e.g. realized by a photo diode). The control unit 20 may then in particular be arranged to control at least one treatment parameter based on the measured skin color, e.g. light intensity and/or pulse length. The sensor 30 is to be understood as an optional feature.

The control unit 20 is here also coupled with a user interface 40, 50, 60, 70 allowing the user to control aspects of the light emission unit 10. The user interface here comprises four input elements 40, 50, 60, and 70. A first input element 40 may be arranged as an ON/OFF switch. A second input element 50 may be arranged as a switch to choose a treatment type, e.g. the second input element 50 may allow a user to switch between a hair removal function and a skin rejuvenation function. The control unit 20 may then be arranged to control at least one treatment parameter based on the chosen type of treatment, e.g. the radiant flux emitted by the LED dies may be lower for a skin rejuvenation function than for a hair removal function. A third input element 60 may be arranged to allow the user to input the hair color. The control unit 20 may then be arranged to control at least one treatment parameter in dependence on the hair color. A fourth input element 70 may be arranged to allow the user to set a maximum radiant fluence value to be applied onto the skin (e.g. a value in the range of between 3 J/cm$^2$ and 7 J/cm$^2$). The control unit 20 may then be arranged to apply only light pulses with a radiant fluence not higher than the chosen maximum radiant fluence. Additionally or alternatively, one of the input elements may be arranged to allow the user to switch from a first active area of the mounted LED dies to second active area (see description with reference to FIGS. 4A and 4B below). Each of the input elements 40, 50, 60, or 70 may be arranged as an input knob or a slider or as a touch sensitive switch on a touch sensitive board. In contrast of being wire-connected with the control unit 20, the user interface may be realized on a separate device that is connected with the control unit 20 in a wireless manner. Instead of four input elements as shown in FIG. 3, the user interface may have one, two, three, five, six or any number of input elements. In some embodiments, the light emission unit 10 is free of any user interface and may be arranged to operate in an automated manner. Other or additional functions than the functions as described above may be realized via the user interface.

FIG. 4A shows one example arrangement of a plurality of LED dies 102 and 103 mounted on a substrate 100A. A plurality of first LED dies 102 has 57 members. A plurality of second LED dies 103 has seven members. The seven members of the second sub-plurality of second LED dies 103 are identified by their matrix positions as $103_{A1}$, $103_{E1}$, $103_{H1}$, $103_{A5}$, $103_{E5}$, $103_{A8}$, and $103_{H8}$. The first sub-plurality of first LED dies 102 are arranged to emit at a far red or infrared (IR) wavelength (first wavelength), which is essentially invisible to the human eye. The first LED dies are then used for applying a treatment light pulse to a skin surface. The second LED dies 103 may then be arranged to emit in the visible wavelength range of between 400 nm and 700 nm (second wavelength different to first wavelength), and the second LED dies may in particular be arranged as low radiant flux LED dies not suitable for emitting light at an intensity level sufficient for temporal hair removal (e.g. the second LED dies may have a specified forward current of below about 100 mA, in particular of around 50 mA or 20 mA at around 2 V supply voltage). In addition or alternatively, the second LED dies may be used to indicate an active area of the LED die matrix. Switched on second LED dies $103_{A1}$, $103_{E1}$, $103_{A5}$, and $103_{E5}$ then indicate that only the first LED dies arranged between those four second LED dies will be used for applying light to the skin (the first active area A1 is indicated by a dashed line), while switched on second LED dies $103_{A1}$, $103_{H1}$, $103_{A8}$, and $103_{H8}$ indicate that the full first sub-plurality of first LED dies will be used (the second active area A2 is indicated by a dashed-dotted line). The smaller first active area A1 may be useful for facial skin treatment (the smaller active area A1 allows more precisely targeting small facial regions), while the larger active area A2 may be useful for body skin treatment (faster treatment). As already mentioned above, an input element may be provided to allow a user to switch between the possible active areas. Depending on the pattern of the LED dies, at least two second LED dies may be used to indicate the active area (e.g. the second LED dies may be arranged in the opposite corners of a square or rectangular arrangement). In some embodiments, the active area of first LED dies may be surrounded by second LED dies to indicate the active area.

Generally, in some embodiments, just a single second LED die is mounted on the substrate (e.g. a plurality of 63 first LED dies is mounted on the substrate in an 8 times 8 matrix as shown in FIG. 4A and only one second LED die). The second LED die may in particular be arranged to emit light in the visible wavelength range (i.e. in between 400 nm and 700 nm) at a low radiant flux (e.g. below 100 mW, typically with a forward current of around 20 mA to 50 mA). Such a second LED die may be used for illumination purposes: the second LED die is controlled to emit the visible light simultaneously with the emission of the treatment light pulse, which is invisible to the human eye.

In some embodiments, three second LED dies are mounted on the substrate in close spatial relationship, where the three second LEDs each emit at a different visible wavelength (e.g. at around 625 nm, 520 nm, and 465 nm—thus the three second LED dies essentially provide the functionality of an RGB LED) so that individual intensity control of the three second LED dies will allow to customize the overall light color that is emitted by the three second LED dies. Such second LED dies may be used for illumination purposes or just for indicating visually that an otherwise non visible light pulse (not visible as being in the invisible IR wavelength range) is emitted onto the skin. An input element may be provided so that a user can set the favored color. In addition, such at least one second LED die to be used for illumination purposes can be present in addition to the second LED dies used for identification of the active size of the first LED die array.

FIG. 4B shows an example embodiment of an four times fifteen LED die matrix mounted on a substrate 100AA similar to the embodiment shown in FIG. 4A, where in addition to a plurality of 54 first LED dies 102A arranged for emitting treatment light pulses a plurality of six second LED dies 103A is arranged to emit light in the visible wavelength range in order to indicate a first active area A3 or a larger second active area A4. Such a rectangular LED die array may in particular be used in a hair removal device that is continuously moved over the skin instead of being subsequently moved from one skin treatment area to another skin treatment area, for which an LED die array as shown in FIG. 4A may be used. The gliding movement may in particular happen in a direction perpendicular to the long axis of the rectangular LED die array. In some embodiments, a glidingly utilized hair removal device may comprise a speed sensor for determining the speed by which the device is moved across the skin. The hair removal device may then be arranged to control the time period between consecutive treatment light pulses in dependence on the determined gliding speed, so that the treatment light pulses are seamlessly applied onto the skin (i.e. essentially without gaps or overlap). Due to the rectangular shape, the smaller active area A3 covers the full width of the LED matrix, which helps in a precise positioning of the small active area A3 onto the treatment area.

FIG. 5 shows an example embodiment of an 8 times 8 matrix of LED dies, where a first sub-plurality of thirty-two first LED dies 104 and a second sub-plurality of thirty-two first LED dies 105 are mounted on a substrate 100B in a checkerboard pattern (e.g. leading to an essentially homogeneous distribution of the first and of the second LED dies over the mounted substrate area). In particular in cases where the array of mounted LED dies is located close to the skin to be treated during operation, an essentially homogeneous illumination can be achieved by either activating only the first sub-plurality of first LED dies or the second sub-plurality of second dies. The first sub-plurality of LED dies 104 may be arranged to emit light at a first wavelength such as 850 nm (in particular at an intensity level sufficient for at least temporal hair removal) and the second sub-plurality of second LED dies may be arranged to emit at a second wavelength different to the first wavelength, e.g. the second wavelength may be 730 nm. The second sub-plurality of first LED dies may emit at a radiant flux that is alone also sufficient for at least temporal hair removal, but the second LED dies may also emit at a radiant flux that is sufficient for hair removal. Instead of being arranged in a checkerboard pattern, the first and second sub-pluralities of first LED dies may also be arranged in any other pattern and there may be more or less first LED dies from the first sub-plurality than first LED dies from the second sub-plurality (e.g. two, seven, ten, sixteen, twenty, forty etc.). As had been mentioned before, the here depicted eight times eight matrix is just for illustration purposes and any arbitrary number of first LED dies may be arranged in any arbitrary pattern, as long as at least the first LED dies are arranged to generate a radiant fluence of at least 3 J/cm$^2$ on the skin during regular operation in a pulse having a pulse length of between 60 ms to 120 ms.

FIG. 6 shows another example embodiment of an 8 times 8 matrix of LED dies mounted on a substrate 100C, where four different pluralities of LED dies are mounted on the substrate 100C. A first sub-plurality of twenty first LED dies 106, a second sub-plurality of twenty-one first LED dies 107, and a third plurality of twenty-one third LED dies 108 are mounted on the substrate in an alternating fashion. In the center of the LED die array two second LED dies 109 are mounted that are arranged to emit in a visible wavelength range at a radiant flux suitable for illumination purposes. In some embodiments, the first sub-plurality of first LED dies 106 may be arranged to emit at a first wavelength (e.g. at 850 nm), the second sub-plurality of first LED dies 107 may be arranged to emit at a second wavelength different to the first wavelength (e.g. 730 nm) and the plurality of third LED dies 108 may be arranged to emit at a third wavelength (e.g. 505 nm) different to the first and second wavelength.

Figure 7A:
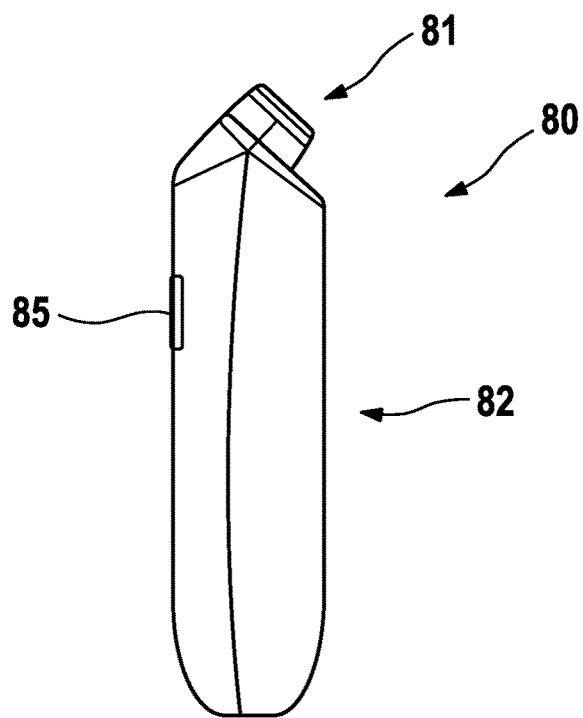
FIG. 7A is a side view of an example embodiment of a hair removal device in accordance with the present disclosure.
Figures 7B, 7C, 7D:
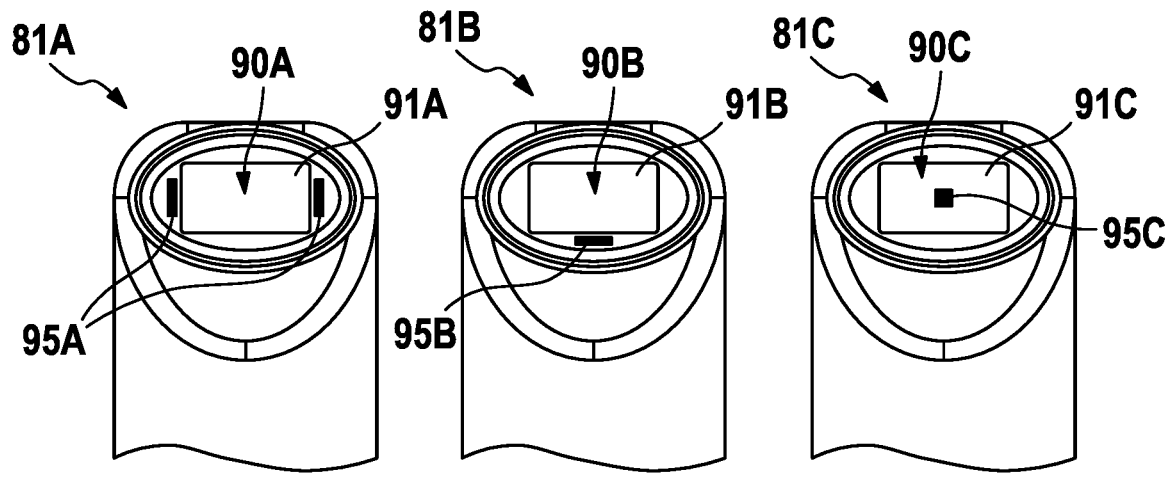
FIGS. 7B-D are front views onto various example head sections of a hair removal device as shown in FIG. 7A, where different positions of one or more additional sensors for measuring a skin property is indicated.

FIG. 7A shows a depiction of a hair removal device 80 in accordance with the present invention. A light emission unit as described in the previous paragraphs is used in the hair removal device 80. The hair removal device 80 has a head section 81 for emission of treatment light pulses and a handle section 82 for holding of the hair removal device 80 by a user's hand. A control element 85 is arranged at the handle section 82 for at least switching ON/OFF the hair removal device 80. FIGS. 7B to 7D show front views of different embodiments of the head section 81A, 81B, 81C, where the embodiments differ essentially only in the location of a sensor or several sensors 95A, 95B, 95C for measuring at least one skin property. The head sections 81A, 81B, 81C each have a respective exit opening 90A, 90B, or 90C through which the treatment light pulses will be emitted during operation. A substrate with a plurality of LED dies mounted on the substrate may be arranged closely behind the exit opening 90A, 90B, 90C or the substrate may be arranged with a certain distance of about or less than 10 mm to the exit opening 90A, 90B, 90C inside of the head section 81A, 81B, 81C. An exit window 91A, 91B, 91C made from a material being essentially transparent to the light to be emitted by the LED dies covers the exit opening 90A, 90B, 90C. The exit opening 90A, 90B, 90C may have a size in the range of between 0.2 mm$^2$ to 10 cm$^2$, in particular in the range of 1 cm$^2$ to 4 cm$^2$. The mounted area of the substrate may then have the same size and shape as the exit opening 90A, 90B, and 90C. In some embodiments, no exit window 91A, 91B, 91C is present. In the embodiment of FIG. 7B, the hair removal device comprises two sensors 95A for measuring at least one skin property, which two sensors 95A are arranged on two opposite sides of the exit opening 90A. In the embodiments shown in FIGS. 7C and 7D, only a single sensor 95B and 95C, respectively, for measuring at least one skin property is arranged on the head section 81B and 81C, respectively. In FIG. 7C, the sensor 95B is arranged underneath the exit opening 90B, so that the sensor 95B is arranged before the exit opening 90B with respect to the usual movement direction (the device in accordance with FIG. 7C may be used in gliding mode). In FIG. 7D, the sensor 95C is arranged in a center area of the exit opening 90C. In such a case, the substrate disposed close to the exit opening 90C may have a respective cutout so that the sensor can be arranged in the cutout or can operate through the cutout. The sensor or sensors 95A, 95B, 95C may also allow determining skin contact, so that a control unit of the light emission unit may be arranged to only trigger the emission of a treatment light pulse in case a skin contact is determined.

Figure 8:
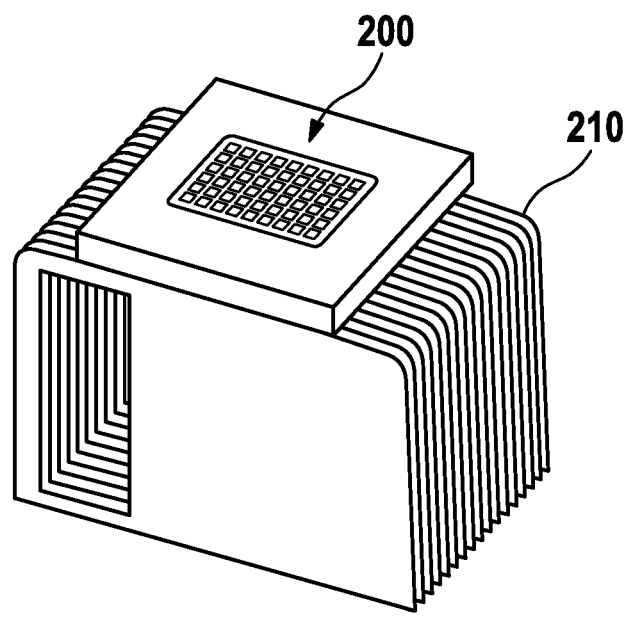
FIG. 8 is a schematic depiction of an array of LED dies mounted on a substrate, which substrate is in turn mounted on a heat sink to carry away excess heat.

FIG. 8 is a depiction of a substrate mounted LED die array 200 that is mounted on a heat sink 210 to convey away excess heat generated by the LED dies in operation. A fan may be arranged close to the heat sink to support the heat dissipation away from the heat sink.

Figure 9A:
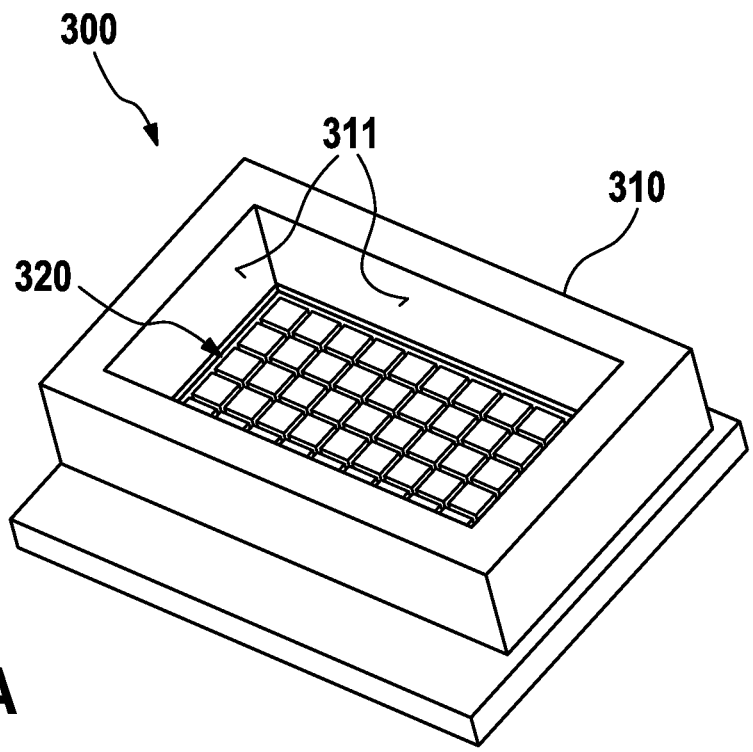
FIG. 9A is a depiction of an array of LED dies mounted on a substrate with a casing having inner reflective walls arranged around the mounted substrate area.
Figure 9B:
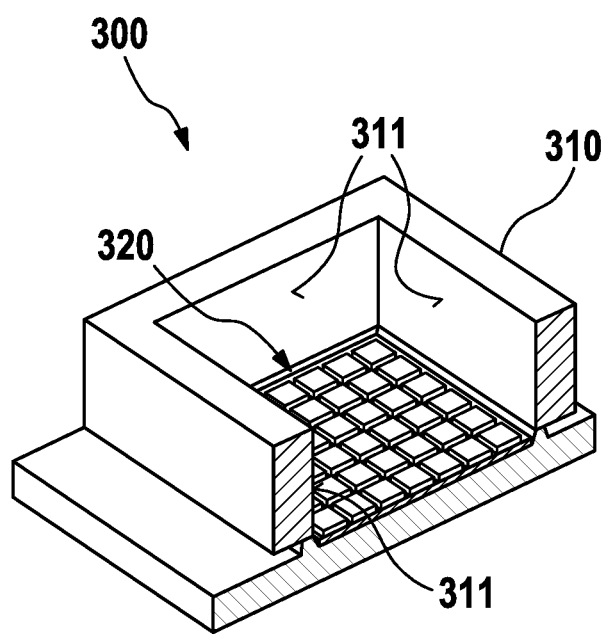
FIG. 9B is a cut-open depiction of the LED array with casing shown in FIG. 9A.

FIGS. 9A and 9B show a perspective view and a cut through a substrate mounted LED die array 300, where a casing 310 is mounted around the mounted area 320. The casing 310 has inner wall surfaces 311 that are highly reflective for the light that is emitted by the LED dies. The inner wall surfaces 311 may have a reflective coating, may be made from polished metal or from a diffusely reflecting plastic or ceramic material. The casing 310 then serves to guide the light emitted by the LED dies in an essentially loss-free manner from the LED die level to an exit opening of the hair removal device and the radiant flux on the level of the LED dies is essentially the same as the radiant flux measured on the treatment area when the exit opening is placed on the skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair removal device comprising a light emission unit comprising a substrate and a plurality of first LED dies that are mounted on the substrate on an area in the range of between about 0.2 cm$^2$ and about 100 cm$^2$, the first LED dies having a peak emission wavelength in the far red or infrared wavelength range of between about 700 nm and about 980 nm, wherein the hair removal device is arranged to emit a treatment light pulse having a pulse length in the range of between about 60 ms and about 120 ms and the first LED dies have a radiant flux such that a radiant fluence on the skin of a user in the range of between about 3 J/cm$^2$ and about 7 J/cm$^2$ is achieved by application of the treatment light pulse.

2. The hair removal device in accordance with claim 1, wherein the first LED dies have a peak emission wavelength in the infrared range of between about 800 nm and about 900 nm.

3. The hair removal device in accordance with claim 1, wherein the first LED dies are mounted on the substrate on an area in the range of between 1.0 cm$^2$ and about 10 cm$^2$.

4. The hair removal device in accordance with claim 2, wherein the first LED dies emit at a peak wavelength of about 850 nm.

5. The hair removal device in accordance with claim 1, wherein the pulse length is in a range of between about 80 ms and about 120 ms.

6. The hair removal device in accordance with claim 1, further comprising a control unit for controlling the plurality of first LED dies and for activating each of the first LED dies to emit light at a selected radiant flux.

7. The hair removal device in accordance with claim 1, wherein at least one second LED die is arranged for emitting light with a peak emission wavelength in the visible wavelength range of between about 400 nm and about 700 nm at a radiant flux lower than the radiant flux required for temporal hair removal.

8. The hair removal device in accordance with claim 4, where the control unit is arranged to control the at least one second LED die to selectively emit visible light at a radiant flux in a range of between about 0.1 mW and about 100 mW also outside of the time period during which a treatment light pulse is emitted.

9. The hair removal device in accordance with claim 1, further comprising a control element for selecting an active area of the plurality of first LED dies mounted on the substrate.

10. The hair removal device in accordance with claim 1, wherein the plurality of first LED dies are mounted on the substrate with a density of at least about 8 LED dies per square centimeter.

11. The hair removal device in accordance with claim 1, wherein the mounted substrate area is surrounded by a casing defining an inner chamber of essentially the shape and area of the mounted substrate area, the casing having inner walls that are reflective with respect to the light emitted by the first LED dies so that the radiant flux of the first LED dies per unit area is essentially preserved until an exit opening of the casing.

12. The hair removal device in accordance with claim 4, wherein the light emission unit comprises at least one sensor for measuring at least one skin property, which sensor is coupled with the control unit for controlling the light emission of at least one first LED die of the plurality of first LED dies based on the measured skin property.

13. The hair removal device in accordance with claim 1, further comprising an exit opening, where each of said first LED dies is separated from the exit opening by a vertical distance in a range of between about 0.1 mm and about 10 mm.

* * * * *